(12) United States Patent
Huang

(10) Patent No.: US 12,392,765 B2
(45) Date of Patent: Aug. 19, 2025

(54) HEATING AND COOLING DEVICE AND PVT EQUIPMENT USING THE SAME

(71) Applicant: U-Can Dynatex Inc., Taichung (TW)

(72) Inventor: Feng-Tsun Huang, Taichung (TW)

(73) Assignee: U-Can Dynatex Inc., Taichung (TW)

( * ) Notice: Subject to any disclaimer, the term of this patent is extended or adjusted under 35 U.S.C. 154(b) by 287 days.

(21) Appl. No.: 18/223,564

(22) Filed: Jul. 19, 2023

(65) Prior Publication Data

US 2024/0027422 A1 Jan. 25, 2024

(30) Foreign Application Priority Data

Jul. 19, 2022 (TW) .................. 111207767

(51) Int. Cl.
*G01N 33/44* (2006.01)
*G01N 3/12* (2006.01)
*G01N 3/60* (2006.01)
*G01N 11/00* (2006.01)

(52) U.S. Cl.
CPC ............. *G01N 33/442* (2013.01); *G01N 3/12* (2013.01); *G01N 3/60* (2013.01); *G01N 2203/0019* (2013.01); *G01N 2203/0411* (2013.01); *G01N 2203/0641* (2013.01); *G01N 2203/0682* (2013.01); *G01N 2203/0694* (2013.01)

(58) Field of Classification Search
CPC .......... G01N 33/442; G01N 3/12; G01N 3/60; G01N 2203/0019; G01N 2203/0411; G01N 2203/0641; G01N 2203/0682; G01N 2203/0694; G01N 25/00; G01N 3/18; G01N 25/20; G01N 3/02; G01N 25/14; G01N 23/20033; G01R 31/2875; G01R 31/2874; G01R 31/2601; G01R 31/2877; G01R 1/0408; G01R 31/2849; H01L 21/67103; G01M 7/02; G01K 15/005; G01K 13/028
USPC ............................................ 73/866; 242/571
See application file for complete search history.

(56) References Cited

U.S. PATENT DOCUMENTS 4,206,805 A * 6/1980 Beckett ............... F04B 39/06
165/169
2014/0264021 A1* 9/2014 Atamanchuk ......... H01J 49/062
250/336.1

FOREIGN PATENT DOCUMENTS

DE 102013012759 A1 * 2/2015 ........... F25D 31/005

* cited by examiner

*Primary Examiner* — Brandi N Hopkins

(57) ABSTRACT

A heating and cooling device includes a conductive structure, an electric heating pipe and a housing. The housing has a main body and a test space formed in the main body, the electric heating pipe is attached on the main body and used for heating a testing plastic material in the test space, and the housing is covered outside the conductive structure and separated from the main body to form a cooling flow channel. The housing and the main body are separated without contacting each other, so that the dissipation of the heat energy of the electric heating pipe through the housing can be reduced in the heating process, and the function of thermal preservation can be provided. Moreover, the cooling effect can be improved through the larger cooling flow channel during the cooling process. A PVT equipment using the heating and cooling device is further provided.

11 Claims, 5 Drawing Sheets

HEATING AND COOLING DEVICE AND PVT EQUIPMENT USING THE SAME

RELATED APPLICATION

This application claims the benefit of priority of Taiwan Patent Application No. 111207767 filed on Jul. 19, 2022, the contents of which are incorporated by reference as if fully set forth herein in their entirety.

BACKGROUND

1. Technical Field

The present disclosure relates to a pressure-volume-temperature (PVT) measurement technology of plastic material, and more particularly, to a heating and cooling device and PVT equipment using the same.

2. Description of Related Art

The PVT measuring instrument is used to measure the rheologic performance of the plastic material to be tested, such as polymer materials, to provide corresponding data. Specifically, the PVT measuring instrument mainly controls the test parameters of heating, cooling and pressure of the plastic material to be tested, so as to know the rheologic properties of the plastic material to be tested, such as stress, deformation, deformation rate, viscosity, etc. during the testing process.

In the current PVT measuring instrument, there is usually a heating and cooling unit that provides heating and cooling functions respectively during the heating and cooling process of the plastic material to be tested, wherein the heating and cooling unit is usually provided with a groove inside, so that the heating pipe is installed in the groove. Accordingly, the plastic material to be tested is heated via the heating pipe during the heating process, and the cooling effect is provided by guiding the airflow in the groove during the cooling process. However, in the heating and cooling unit of the current PVT measuring instrument, only the groove provided with the heating pipe is used to introduce the airflow, that is, the airflow can only pass through the narrow groove to cool down the plastic material to be tested, so the amount of the introduced airflow is quite limited, which will cause the problem of poor cooling effect (such as cooling too slow); moreover, the current PVT measuring instrument does not have the design to keep the heating and cooling unit warm, so the heating effect is not good due to the leakage of the heat source during the heating process; furthermore, in the current PVT measuring instrument, the stability of the machine of the PVT measuring instrument is not good due to the poor design of struts, such that the machine of the PVT measuring instrument may shake during the pressurization process which may result in an inaccurate measurement. Therefore, there is still much room for improvement in current PVT measuring instruments.

In light of the above, a design should be found to improve the capacity for heating and cooling and stability of the PVT equipment, in particular, by providing a better testing environment for the plastic material to be tested, so as to achieve an effect of effective and rapid cooling, maintaining the temperature of the plastic material to be tested and strengthening the stability of the machine, which will become the technical goal that those persons skilled in the art are striving for.

SUMMARY

In view of the aforementioned shortcomings of the prior art, the present disclosure provides a heating and cooling device disposed in a pressure-volume-temperature equipment and used to heat and cool a testing plastic material, the heating and cooling device comprises: a conductive structure comprising a main body and a test space formed in the main body for placing the testing plastic material; an electric heating pipe attached on the main body for heating the testing plastic material in the test space through the main body; and a housing disposed outside the conductive structure and separated from the main body to form a cooling flow channel, wherein the housing has an air inlet and an air outlet for cooling airflow to enter and exit the cooling flow channel to cool the testing plastic material.

In one embodiment, the main body further comprises a sensing hole recessed in a direction from an outer sidewall of the main body to the test space for disposing a sensor.

In another embodiment, an outer sidewall of the main body has a groove, and the electric heating pipe is accommodated in the groove and attached on the main body.

In another embodiment, the groove is spiraled around the main body.

In another embodiment, the main body further comprises a cover plate extending radially from two ends of the main body to the housing.

In another embodiment, the air inlet and the air outlet are disposed at opposite ends of the housing respectively.

In yet another embodiment, the main body is penetrated through by the test space.

The present disclosure further provides a pressure-volume-temperature equipment, which comprises: the abovementioned heating and cooling device; and a testing machine comprising a carrier for disposing the heating and cooling device, and a plunger rod located above the carrier and used to enter and exit the test space, wherein a pressure-volume-temperature detection is performed on the testing plastic material in the test space when the plunger rod enters downward into the test space.

In one embodiment, the carrier comprises a heat insulation structure at a bottom of the carrier, and the heating and cooling device is disposed on the carrier via the heat insulation structure.

In another embodiment, the testing machine further comprises: a pressure plate on which the plunger rod is disposed; a load cell located between the pressure plate and the plunger rod; and a plurality of struts on which the pressure plate is movably disposed, so that the pressure plate is moved up and down relative to the carrier.

In another embodiment, a number of the plurality of struts is four.

In yet another embodiment, the pressure-volume-temperature equipment of the present disclosure further comprises: a servo motor located at a top of the testing machine for driving the pressure plate to move on the plurality of struts; and an optical ruler disposed at a side of the testing machine for measuring a height change of the plunger rod relative to the carrier.

In view of the above, the heating and cooling device heats the test space by the electric heating pipe through the main body of the conductive structure during the heating process, and since the housing and the main body of the present disclosure are separated from each other, a larger cooling flow channel can be formed, so as to achieve the purpose of improving the cooling effect during the cooling process; further, the pressure-volume-temperature equipment of the present disclosure is provided with a heat insulation structure for the installation of the heating and cooling device, so that the heat energy generated in the heating process can be prevented from being dissipated through the carrier, and the thermal preservation function in the heating process can be achieved. And the pressure-volume-temperature equipment uses four struts which can improve the stability of the plunger rod during movement and pressurization.

DETAILED DESCRIPTION

Implementations of the present disclosure are described below by embodiments. Other advantages and technical effects of the present disclosure can be readily understood by one of ordinary skill in the art upon reading the disclosure of this specification.

Figure 1:
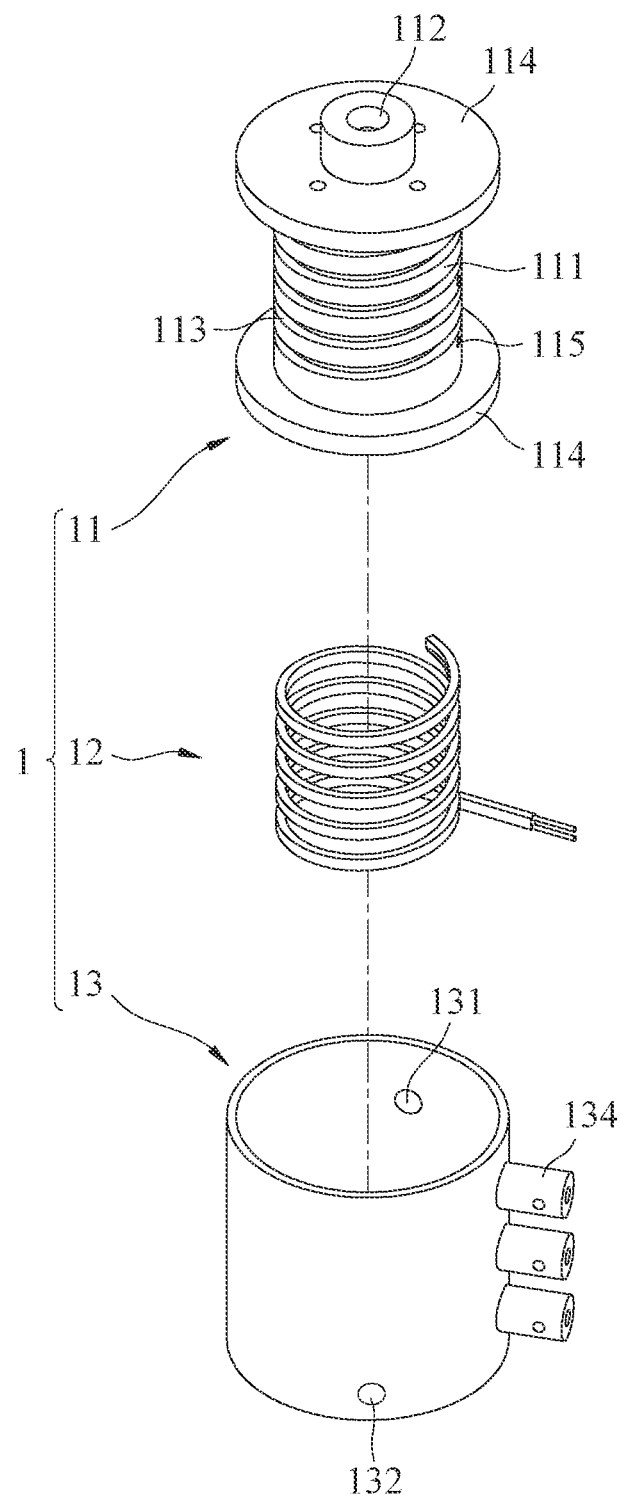
FIG. 1 is an exploded perspective view of a heating and cooling device of the present disclosure.
Figure 2:
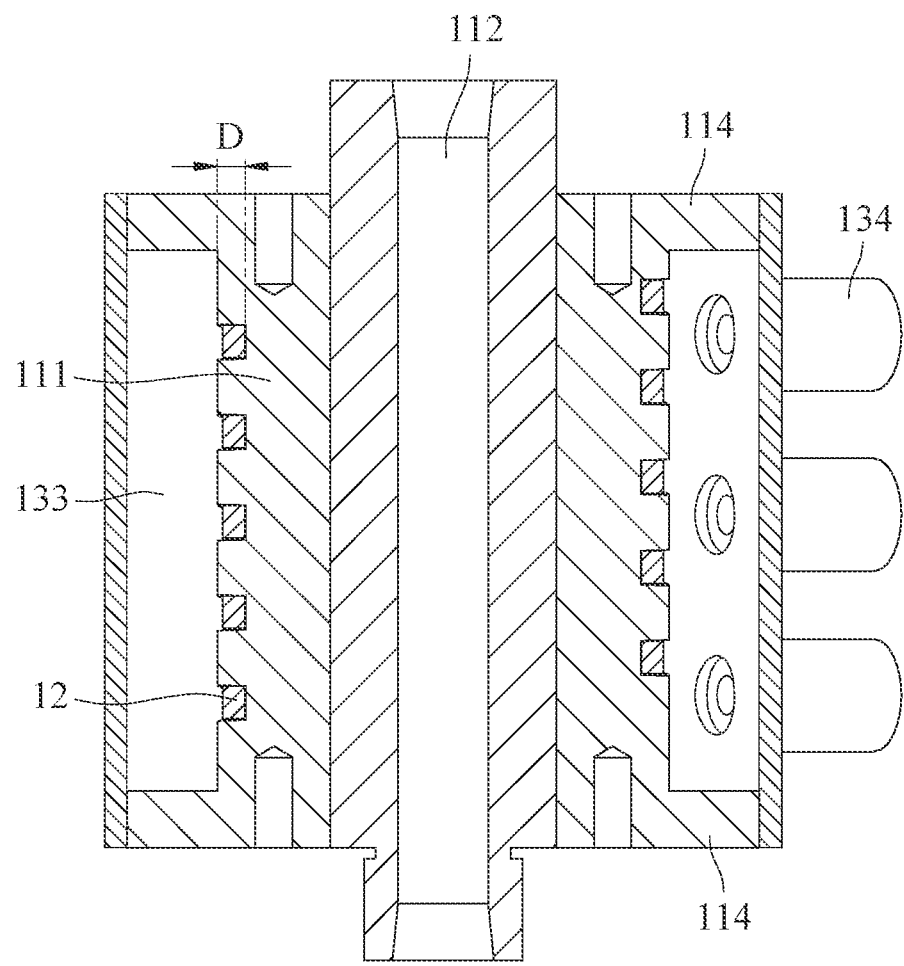
FIG. 2 is a side cross-sectional view of the heating and cooling device of the present disclosure.

FIG. 1 is an exploded perspective view of a heating and cooling device of the present disclosure, and FIG. 2 is a side cross-sectional view of the heating and cooling device of the present disclosure. As shown in FIG. 1 and FIG. 2, a heating and cooling device 1 of the present disclosure is disposed in a PVT equipment for heating and cooling a testing plastic material with a pressure-volume-temperature (PVT) detection. Specifically, the heating and cooling device 1 of the present disclosure comprises a conductive structure 11, an electric heating pipe 12 attached on the conductive structure 11 and a housing 13 disposed outside the conductive structure 11, wherein the conductive structure 11 is provided for placing the testing plastic material therein, so that the testing plastic material is heated by a heat generated by the electric heating pipe 12 and through the conductive structure 11 during the heating process, and a cooling airflow is introduced from the outside of the housing 13 during the cooling process, so that the cooling airflow can dissipate heat from the testing plastic material in the conductive structure, and then the cooling airflow is discharged. In this way, the heating and cooling device 1 can achieve the purpose of heating and cooling the testing plastic material, so as to facilitate the pressure-volume-temperature detection of the PVT equipment. The following is a detailed description of the present disclosure.

The conductive structure 11 comprises a main body 111 and a test space 112 formed in the main body 111. Specifically, the main body 111 is cylindrical, and the test space 112 is formed longitudinally along the axis of the main body 111. In one embodiment, the test space 112 is formed by longitudinally penetrating through the main body 111, and a lower part is sealed by other accessories for placing the testing plastic material therein. In another embodiment, the outer sidewall of the main body 111 is recessed inward to form a groove 113, so that the electric heating pipe 12 can be accommodated in the groove 113 and attached on the main body 111; and further, the groove 113 may have a spiral shape, that is, the groove 113 can be spiraled around on the main body 111. In addition, the upper and lower ends of the main body 111 may have cover plates 114 radially extending to the inner sidewall of the housing 13, so that an airtight space is formed between the housing 13 and the two cover plates 114 when the conductive structure 11 is disposed inside the housing 13. The airtight space reduces the outflow of hot air during the heating process; and the airtight space is used as a flow channel to introduce/guide the airflow during the cooling process, thereby effectively providing the cooling effect.

In another embodiment, the main body 111 further comprises a sensing hole 115 recessed to a direction from the outer sidewall to the test space for disposing a sensor in the sensing hole 115. More specifically, as shown in FIG. 1, the sensing hole 115 is adjacent to the test space 112 but not in communication with the test space 112, and the sensing hole 115 can be used to accommodate, for example, a sensor for sensing temperature, so as to measure the real-time temperature of the test space 112 during the heating process or the cooling process to provide corresponding measurement data.

The electric heating pipe 12 is attached on the main body 111 to heat the testing plastic material in the test space 112 through the main body 111 of the conductive structure 11 during the heating process. In one embodiment, the electric heating pipe 12 can be disposed in the groove 113 and surround on the main body 111. The electric heating pipe 12 spirally surrounds on the main body 111 along the groove 113 as the groove 113 has a spiral shape, so that the main body 111 conducts heat energy to the test space 112 when being heated to heat the testing plastic material contained in the test space 112.

The housing 13 is covered outside the conductive structure 11, wherein the housing 13 and the outer sidewall of the main body 111 are separated with a distance, that is, the inner sidewall of the housing 13 is free from being in contact with the outer sidewall of the main body 111, so that a cooling flow channel 133 is formed between the housing 13 and the main body 111; in addition, the housing 13 has an air inlet 131 and an air outlet 132 communicating with the cooling flow channel 133, so that the cooling airflow is introduced from the air inlet 131 during the cooling process, and the main body 111 is cooled down after the cooling airflow enters the cooling flow channel 133 and flows through the main body 111, and then a heated airflow flowed through the main body 111 is discharged from the air outlet 132.

In one embodiment, the air inlet 131 and the air outlet 132 may be disposed at opposite ends of the housing 13, that is, the air inlet 131 and the air outlet 132 are located at an upper end and a lower end of the housing 13 in a manner of one above the other, so that the airflow flowing through the cooling flow channel 133 effectively cools down the main body 111.

In addition, as shown in FIG. 1 and FIG. 2, in the present disclosure, the dissipation of the heat energy to outside through the housing 13 may be reduced during the heating process since the main body 111 is free from being in contact with the housing 13. The large cooling flow channel 133 can make a large amount of cooling airflow flow from the air inlet 131 to the main body 111 during the cooling process, so as to achieve a good cooling effect. In addition, in the present disclosure, the main body 111 can be formed into a structure similar to heat dissipation fins by controlling the extent to which the groove 113 is recessed into the main body 111, such as deepening a depth D of the groove 113 (as shown in FIG. 2), so as to increase heat dissipation area to provide better heat dissipation effect.

In one embodiment, the housing 13 is further arranged with a channel 134 relative to the sensing hole 115 of the conductive structure 11, so that the sensor can be disposed in the sensing hole 115 through the channel 134 of the housing 13 to measure the temperature change of the test space 112.

In one embodiment, the testing plastic material of the present disclosure is a plastic such as a thermoplastic.

Figure 3:
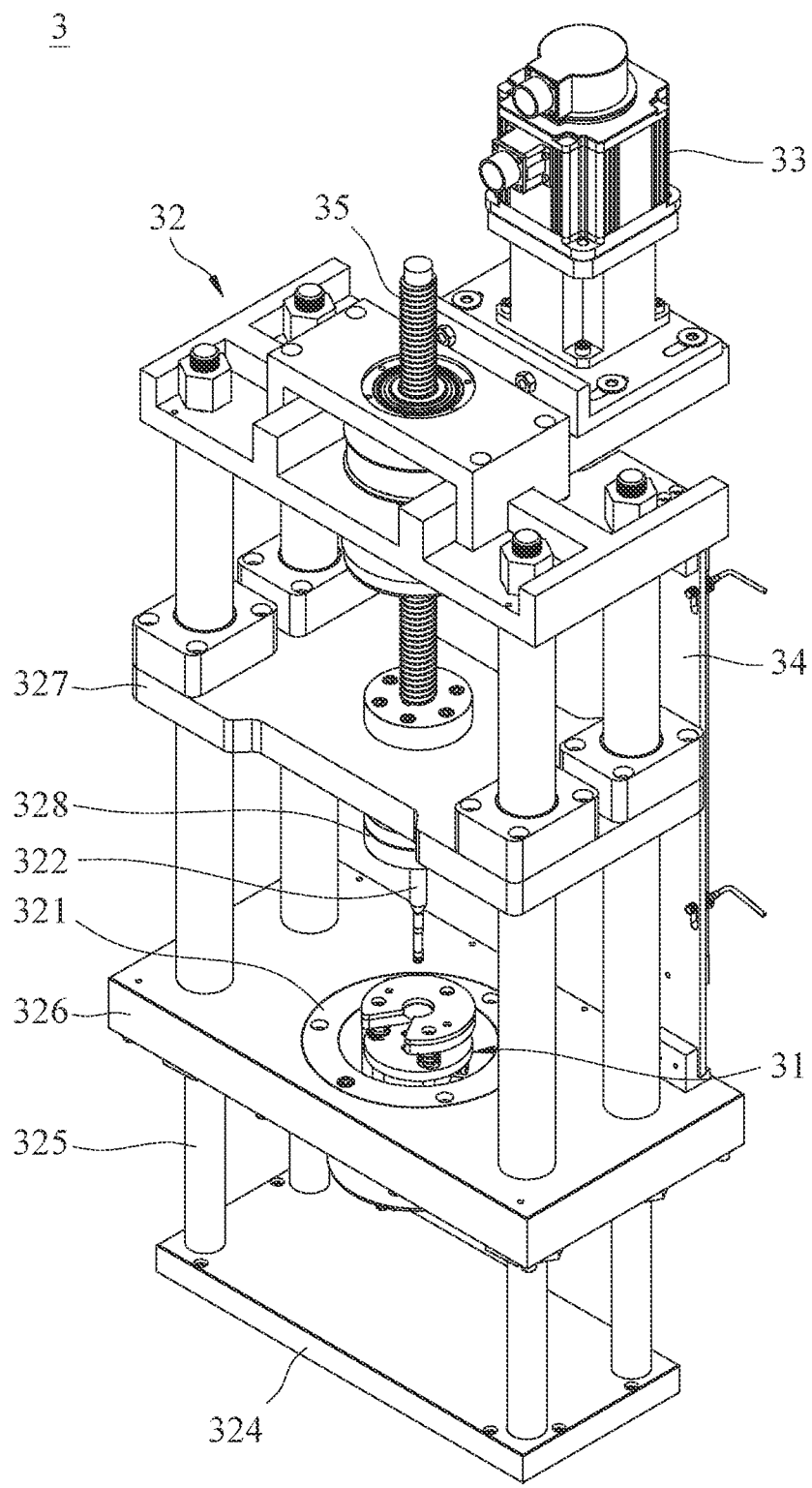
FIG. 3 is a perspective view of the structure of a PVT equipment of the present disclosure.
Figure 4A:
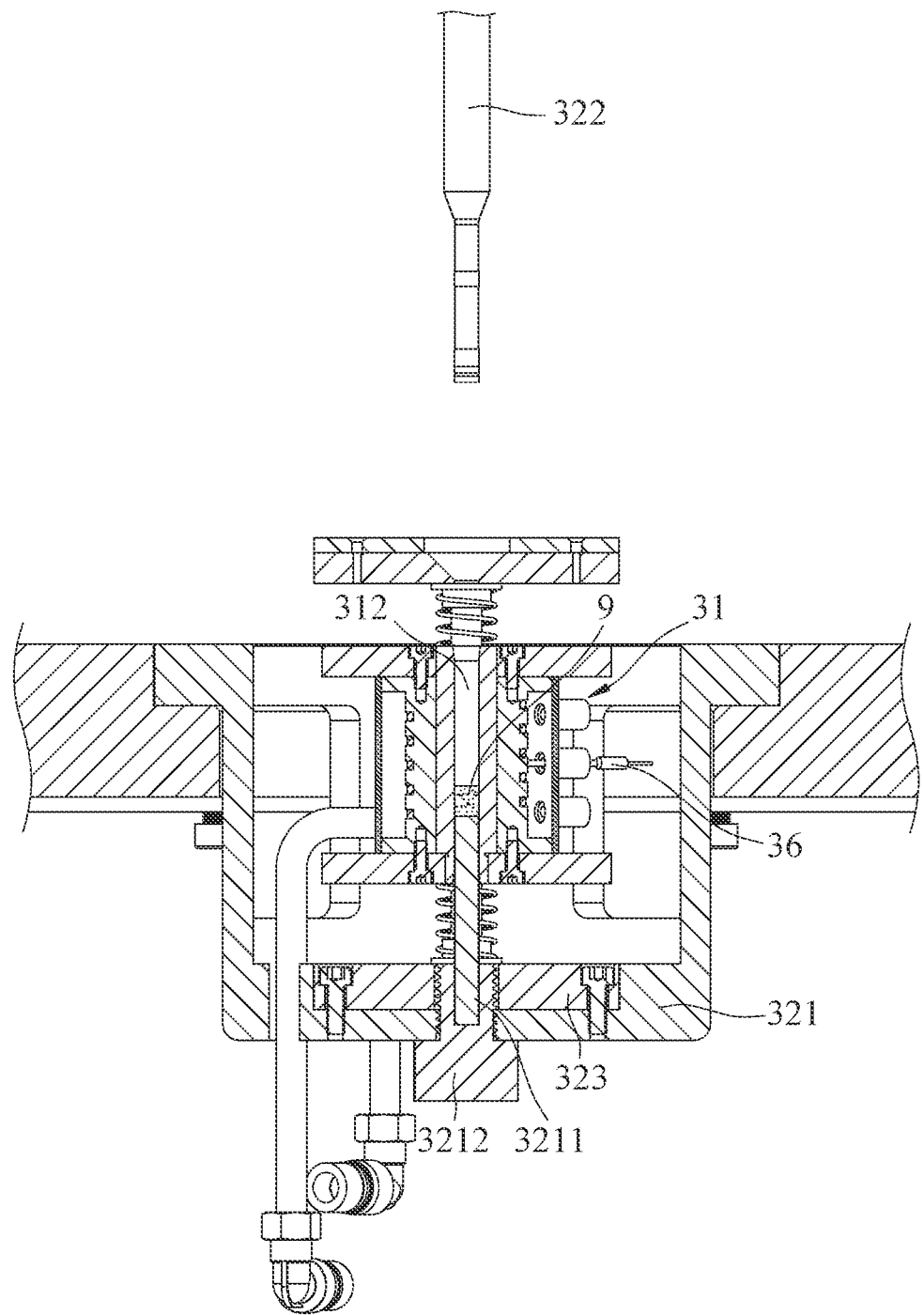
FIG. 4A and FIG. 4B are partial cross-sectional views of the PVT equipment of the present disclosure during the actuation.
Figure 4B:
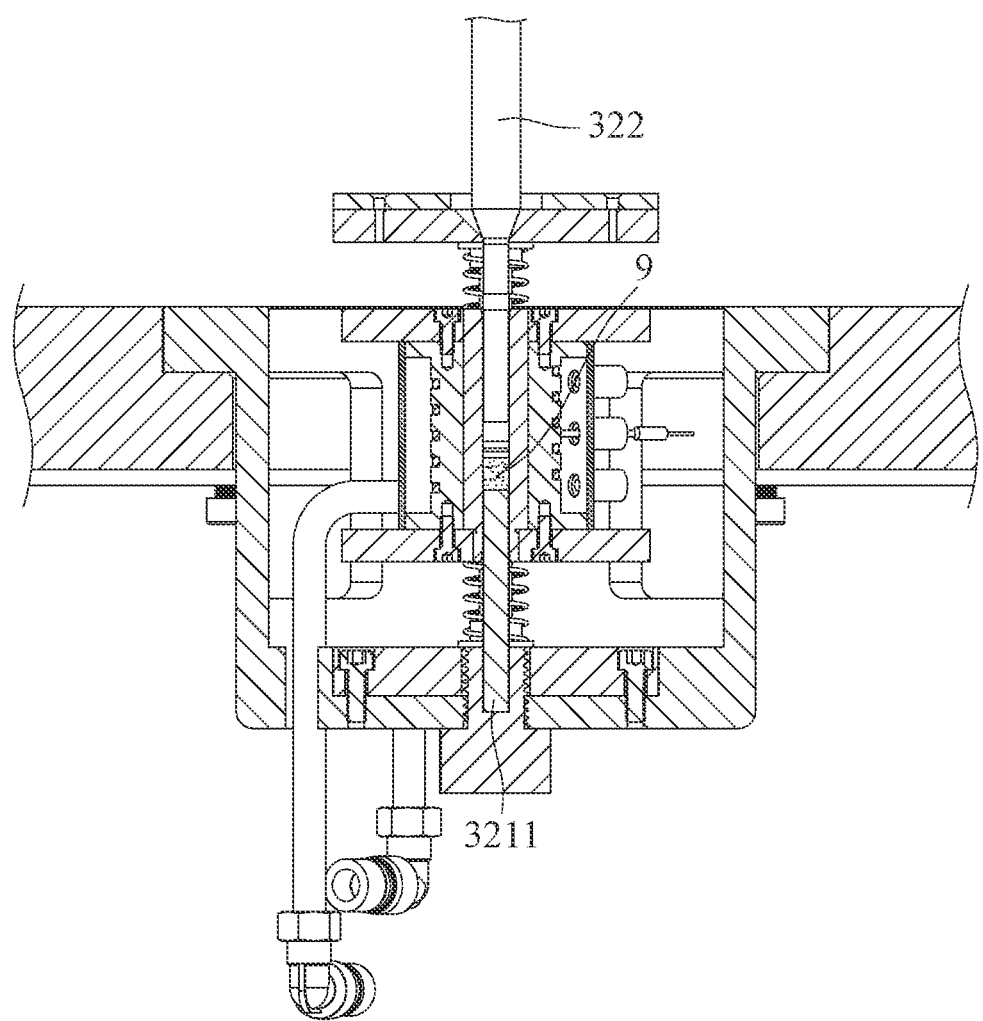

FIG. 3 is a perspective view of the structure of the PVT equipment of the present disclosure, and FIG. 4A and FIG. 4B are partial cross-sectional views of the PVT equipment of the present disclosure during the actuation. As shown in FIG. 3, FIG. 4A and FIG. 4B, a PVT equipment 3 of the present disclosure comprises a heating and cooling device 31 for heating or cooling a testing plastic material 9, and a testing machine 32 for disposing the heating and cooling device 31 to measure the pressure-volume-temperature (PVT) of the testing plastic material 9. The PVT equipment 3 of the present disclosure is detailed as below.

The heating and cooling device 31 is used to accommodate the testing plastic material 9, so as to heat and melt the testing plastic material 9 during the heating process, and provide a cooling effect during the cooling process. In one embodiment, the present disclosure utilizes the heating and cooling device 31 described above (as shown in FIG. 1 and FIG. 2) to provide the function of heating or cooling the testing plastic material 9. The detailed description of the heating and cooling device 31 is as stated above, and will not be described herein.

The testing machine 32 comprises a carrier 321 (e.g., a carrying base) for disposing the heating and cooling device 31, and a plunger rod 322 located above the carrier 321 and used to enter and exit a test space 312 of the heating and cooling device 31. As shown in FIG. 4A, in one embodiment, the carrier 321 comprises a heat insulation structure 323 disposed on a bottom thereof for blocking thermal conduction, so that the heating and cooling device 31 is disposed on the carrier 321 via the heat insulation structure 323.

Specifically, the testing machine 32 further comprises a base 324, a plurality of struts 325 fixed on the base 324, a testing platform 326 located above the base 324 and fixed on each of the struts 325 for disposing the carrier 321, a pressure plate 327 located above the testing platform 326 and movably provided on the plurality of struts 325 and for the plunger rod 322 to be provided below, and a load cell 328 disposed between the pressure plate 327 and the plunger rod 322, wherein the load cell 328 is used for sensing pressure.

In addition, the PVT equipment of the present disclosure further comprises a servo motor 33 located at a top of the testing machine 32 and an optical ruler 34 disposed on a side of the testing machine 32 for measuring a height of the plunger rod 322 relative to the carrier 321, wherein the pressure plate 327 is disposed on the plurality of struts 325 in a manner of moving up and down relative to the carrier 321. Accordingly, the testing machine 32 uses the servo motor 33 to drive the pressure plate 327 to move on the plurality of struts 325 via a screw rod 35, and uses the optical ruler 34 to measure the height of the plunger rod 322 relative to the carrier 321, and then calculates the volume change from the height change. It should be noted that the setting of the optical ruler 34 is not limited in the above way, as long as the height change between the plunger rod 322 and the carrier 321 can be measured.

In one embodiment, the testing machine 32 of the present disclosure may have four struts 325, so as to provide a better stability during the movement of the pressure plate 327 and the plunger rod 322.

As shown in FIG. 4A, a lower pushing post 3211 (e.g., a lower holding post) is disposed on the carrier 321 from bottom to top to penetrate into the test space 312 before the testing plastic material 9 is tested, and the lower pushing post 3211 is fixed with a screw 3212 (e.g., a pushing/holding screw) under the lower pushing post 3211 to seal the bottom of the test space 312, so that the test space 312 can be filled with the testing plastic material 9. Before the testing plastic material 9 is placed, the heating and cooling device 31 is preheated via an electric heating pipe, that is, a heating process is performed. After the test space 312 is heated to the initial temperature through the main body, the testing plastic material 9 is put into the test space 312, such that the testing plastic material 9 is heated to melt.

Next, as shown in FIG. 4B, when the test space 312 is filled with the testing plastic material 9, the testing machine 32 uses the servo motor 33 to drive the pressure plate 327 to descend, so that the plunger rod 322 is inserted downward into the test space 312 and the testing plastic material 9 is pressurized, and the test space 312 is sealed up and down by the lower pushing post 3211 and the plunger rod 322 to form a sealed space, thereby generating the required pressure; further, when cooling is required, an external cooling airflow is introduced through the air inlet of the housing to form a circulating airflow in the cooling flow channel, so that the airflow will flow through the main body to cool down the main body, and the heated airflow flowing through the main body will be discharged from the air outlet, so as to provide the cooling function, wherein a good cooling effect can be provided since the cooling flow channel designed in the present disclosure is large. When the test time ends, the testing machine drives the pressure plate 327 by the servo motor 33, so that the pressure plate 327 and the plunger rod 322 fixed thereon return to the starting position again (as shown in FIG. 4A), and the test ends.

During the test, the present disclosure measures the relative position or height between the plunger rod 322 and the carrier 321 via the optical ruler 34 to obtain the height change, and calculates the volume change value of the testing plastic material during the test by the height change. In addition, the PVT equipment of the present disclosure is further disposed with, for example, a temperature sensor 36 (as shown in FIG. 4A) in the sensing hole of the main body, so as to measure the temperature change during the test.

In addition, the test of the present disclosure is based on the standard ISO17744, and the volume change of the testing plastic material (e.g., using the optical ruler to measure the change in the height of the plunger rod as mentioned above) is observed and measured by changing the temperature (e.g., using a heating and cooling device to provide heating or cooling functions) or changing the pressure (using a servo motor to drive the plunger rod to pressurize the testing plastic material). Lastly, the temperature value, pressure value obtained during the test and the volume change value of the testing plastic material measured/calculated by the optical ruler are sent back to the remote computer or stored in the local database, so that the data detection related to the pressure-volume-temperature (PVT) of the testing plastic material is completed.

In view of the above, the heating and cooling device of the present disclosure used for PVT equipment forms a larger cooling flow channel instead of a narrow airflow channel by separating the housing and the main body of the conductive structure, and because of most of the area of the main body of the present disclosure is exposed in the cooling flow channel and is free from being in contact with the housing, a larger heat dissipation area can be provided and the heat energy of the electric heating pipe can be prevented from dissipating through the housing during the heating process. Accordingly, the present disclosure can provide a function of thermal preservation to the test space and the testing plastic material during the heating process, and can effectively improve the heat dissipation effect during the cooling process; further, the PVT equipment of the present disclosure has a heat insulation structure for the heating and cooling device, which can prevent the heat energy from being dissipated from the carrier to the environment, thereby achieving the purpose of thermal insulation and preservation; in addition, the testing machine of the present disclosure uses four struts, which can improve the stability of the movement when the pressure plate and the plunger rod are moved during the test.

The above embodiments are provided for illustrating the principles of the present disclosure and its technical effect, and should not be construed as to limit the present disclosure in any way. The above embodiments can be modified by one of ordinary skill in the art without departing from the spirit and scope of the present disclosure. Therefore, the scope claimed of the present disclosure should be defined by the following claims.

What is claimed is:

1. A heating and cooling device disposed in a pressure-volume-temperature equipment and used to heat and cool a testing plastic material, the heating and cooling device comprising:
   a conductive structure comprising a main body and a test space formed in the main body for placing the testing plastic material;
   an electric heating pipe attached on the main body for heating the testing plastic material in the test space through the main body; and
   a housing disposed outside the conductive structure and separated from the main body to form a cooling flow channel, wherein the housing has an air inlet and an air outlet for cooling airflow to enter and exit the cooling flow channel to cool the testing plastic material.

2. The heating and cooling device of claim 1, wherein the main body further comprises a sensing hole recessed in a direction from an outer sidewall of the main body to the test space for disposing a sensor.

3. The heating and cooling device of claim 1, wherein an outer sidewall of the main body has a groove, and the electric heating pipe is accommodated in the groove and attached on the main body.

4. The heating and cooling device of claim 3, wherein the groove is spiraled around the main body.

5. The heating and cooling device of claim 1, wherein the main body further comprises a cover plate extending radially from two ends of the main body to the housing.

6. The heating and cooling device of claim 1, wherein the air inlet and the air outlet are disposed at opposite ends of the housing respectively.

7. The heating and cooling device of claim 1, wherein the main body is penetrated through by the test space.

8. A pressure-volume-temperature equipment, comprising:
   the heating and cooling device of claim 1; and
   a testing machine comprising a carrier for disposing the heating and cooling device, and a plunger rod located above the carrier and used to enter and exit the test space, wherein a pressure-volume-temperature detection is performed on the testing plastic material in the test space when the plunger rod enters downward into the test space.

9. The pressure-volume-temperature equipment of claim 8, wherein the carrier comprises a heat insulation structure at a bottom of the carrier, and the heating and cooling device is disposed on the carrier via the heat insulation structure.

10. The pressure-volume-temperature equipment of claim 8, wherein the testing machine further comprises:
    a pressure plate on which the plunger rod is disposed;
    a load cell located between the pressure plate and the plunger rod; and
    a plurality of struts on which the pressure plate is movably disposed, so that the pressure plate is moved relative to the carrier.

11. The pressure-volume-temperature equipment of claim 10, further comprising:
    a servo motor located at a top of the testing machine for driving the pressure plate to move on the plurality of struts; and
    an optical ruler disposed at a side of the testing machine for measuring a height change of the plunger rod relative to the carrier.

* * * * *